United States Patent [19]

Reinartz et al.

[11] Patent Number: 5,198,550
[45] Date of Patent: Mar. 30, 1993

[54] PROCESS FOR THE PURIFICATION OF CRUDE 2-MERCAPTOBENZOTHIAZOLE

[75] Inventors: Klaus Reinartz, Cologne; Harro Schlesmann, Odenthal; Stefan Dietl, Cologne, all of Fed. Rep. of Germany

[73] Assignee: Bayer Aktiengesellschaft, Leverkusen-Bayerwerk, Fed. Rep. of Germany

[21] Appl. No.: 890,764

[22] Filed: Jun. 1, 1992

[30] Foreign Application Priority Data

Jun. 11, 1991 [DE] Fed. Rep. of Germany ....... 4119184
Aug. 15, 1991 [DE] Fed. Rep. of Germany ....... 4126992

[51] Int. Cl.$^5$ ............................................. C07D 277/72
[52] U.S. Cl. ...................................................... 548/177
[58] Field of Search ............................................ 548/177

[56] References Cited

U.S. PATENT DOCUMENTS 3,770,759 11/1973 Scherhag et al. ................... 548/177
4,316,031 2/1982 Bergfeld et al. ..................... 546/175

FOREIGN PATENT DOCUMENTS 476266 11/1975 U.S.S.R. .

*Primary Examiner*—Mary C. Lee
*Assistant Examiner*—MarySusan H. Gabilan
*Attorney, Agent, or Firm*—Connolly & Hutz

[57] ABSTRACT

Crude 2-mercaptobenzothiazole is purified by a process in which the crude 2-mercaptobenzothiazole is dissolved in relatively high-boiling aliphatic or cycloaliphatic alcohols or in mixtures of the alcohols mentioned or azeotropes thereof with water at temperatures of 60° to 200° C., optionally under elevated pressure, or is suspended in relatively high-boiling aliphatic or cycloaliphatic alcohols, aliphatic or cycloaliphatic ethers, organic acids or esters thereof at temperatures of 10° to 100° C., the solution or suspension is subsequently cooled and the product precipitating is filtered off and optionally washed.

3 Claims, No Drawings

PROCESS FOR THE PURIFICATION OF CRUDE 2-MERCAPTOBENZOTHIAZOLE

This invention relates to a process for the purification of crude 2-mercaptobenzothiazole. The process according to the invention gives good yields of high-purity 2-mercaptobenzothiazole.

Processes for purifying the crude melt of 2-mercaptobenzothiazole have often been described in the literature. Hitherto the most commonly used process comprises dissolving the hot crude melt in a hot alkaline solution and subsequent precipitation by addition of an acid (U.S. Pat. No. 1,631, 871, U.S. Pat. No. 2,137,820, U.S. Pat. No. 2,161,741, DD 233 127). The additional purification of this solution by introduction of air, even in the presence of active carbon (GB 1,321,181), has also been described (U.S. Pat. No. 2,631,153). In a similar process (DOS 2 258 484), the crude 2-mercaptobenzothiazole is first recrystallized from an aromatic hydrocarbon and then dissolved in aqueous sodium hydroxide. In another process, the hot crude melt is first dissolved in an inert solvent and the 2-mercaptobenzothiazole is extracted from this solution with aqueous alkali metal hydroxide solution and precipitated by acidification (DOS 1 941 379). The disadvantages common to all processes lie in the accumulation of a heavily contaminated wastewater and in the large quantities of alkali and acid required because neither can be recycled to the process.

In addition, processes for recrystallizing crude 2-mercaptobenzothiazole are described in the literature. Solvents are used in these processes, including for example aniline (EP 169 107, U.S. Pat. No. 4,647,669), chlorobenzene or nitrobenzene (SU 852 869), hydrocarbons in admixture with 5% phenol and 1% pyridine (DE 541 295), a mixture of acetone, water and sulfuric acid (SU 476 266) or dilute ethanol or 50% acetic acid (J. Prakt. Chem. 93 (1916) 183). Although all these processes are said to give good to very good yields, they are attended either by the disadvantage that strict safety precautions have to be taken or by the disadvantage that working up of the mother liquor is highly cost-intensive. The same also applies to the purification process described in U.S. Pat. No. 3,030,373 and Ca 448 209, in which 2-mercaptobenzothiazole is suspended in a mixture of water and a water-insoluble solvent, such as carbon disulfide, toluene or benzene, at elevated temperature and elevated pressure. Steam distillation (DE 936 039, U.S. Pat. No. 3,658,864, GB 734,970) for the removal of impurities, such as benzthiazole for example, also appears to be a relatively complicated process in this connection.

Liquid/liquid extraction (DOS 2 652 394) also appears to be an extremely complicated process because introduction of the liquid and hence very hot crude melt into cold carbon disulfide requires special safety measures.

The preliminary evaporation step described in DOS 2 022 569 is also not particularly suitable for operation on a large scale, especially since the condensed product has to be further purified - again by dissolution in aqueous sodium hydroxide, extraction of the solution with a water-insoluble solvent and precipitation of the 2-mercaptobenzothiazole by acidification of the aqueous phase.

Suspension of the crude 2-mercaptobenzothiazole in toluene, optionally with addition of pyridine, picoline or aniline, at a temperature of 30° C. (JP 6025979) only gives a product of inferior quality, even after two repetitions. Extraction of the crude 2-mercaptobenzothiazole with carbon tetrachloride or tetrachloroethylene has also been described (JP 7919976). In another known process (JP 6025980), the crude melt is purified by slow crystallization of the melt. The impurities are said to remain in the mother liquor obtained.

A process for the purification of crude 2-mercaptobenzothiazole has now been found and is characterized in that the crude 2-mercaptobenzothiazole is dissolved in relatively high-boiling aliphatic or cycloaliphatic alcohols or in mixtures of the above-mentioned alcohols or azeotropes thereof with water at temperatures of 60° to 200° C. and optionally under elevated pressure, the solution is subsequently cooled and the product precipitating is filtered off and optionally washed.

The advantage of this process lies in the fact that it can readily be carried out on an industrial scale with solvents that are easy to handle and, in addition, shows high selectivity.

The crude 2-mercaptobenzothiazole to be purified is produced from aniline, carbon disulfide and sulfur at elevated temperature and pressure in accordance with U.S. Pat. No. 1,631,871. The 2-mercaptobenzothiazole obtained has a 2-mercaptobenzothiazole content of approximately 80 to 90%.

According to the invention, the crude 2-mercaptobenzothiazole is dissolved in relatively high-boiling aliphatic or cycloaliphatic alcohols or mixtures thereof or azeotropes thereof with water at temperatures of 60° to 200° C., preferably at temperatures of 80° to 165° C. and more preferably at the boiling point of the alcohol used.

Suitable aliphatic or cycloaliphatic alcohols are, for example, isopropanol, n-butanol or cyclohexanol or the isopropanol/water azeotrope. The quantity of alcohol used is gauged so that a saturated solution of the crude 2-mercaptobenzothiazole is obtained in the selected temperature range.

In the purification process according to the invention, pressure (1 to 50 bar) may be applied to dissolve the crude 2-mercaptobenzothiazole in the alcohols mentioned. However, the purification process according to the invention is preferably carried out under atmospheric pressure. If pressure is applied, the process may be carried out in an inert gas atmosphere (nitrogen, noble gases).

Precipitation of the 2-mercaptobenzothiazole dissolved in the alcohols mentioned may be carried out by various methods. One method is slowly to cool the hot solution to temperatures of 0° to 30° C. and preferably to room temperature. The period required for cooling is about 30 minutes to 10 hours and preferably 4 to 6 hours. The 2-mercaptobenzothiazole precipitated may be separated from the mother liquor by filtration.

Another method of precipitating the dissolved 2-mercaptobenzothiazole is partly to distill off the solvent under a reduced pressure of about 0.01 bar to 0.9 bar and preferably 0.1 to 0.8 bar and at a constant temperature. The 2-mercaptobenzothiazole precipitating from this solution may then be filtered off either while still hot or after partial or complete cooling of the solution.

Another method of precipitating the dissolved 2-mercaptobenzothiazole is to allow a hot solution prepared under pressure to expand. The product precipitated may be filtered off both from the hot and also from the partly or completely cooled solution. However, the methods for precipitating the product from the saturated solution are by no means confined to the variants described herein.

The product filtered off may then be washed with a solvent, preferably with an aliphatic or cycloaliphatic alcohol or mixtures thereof, to remove residual adhering mother liquor. Washing may be carried out at temperatures of 0° to 40° C. and preferably at room temperature. For washing, the solvent is normally used in a quantity of 0.1 to 1.0 part by weight and preferably in a quantity of 0.3 to 0.6 part by weight per part by weight crude 2-mercaptobenzothiazole used.

Subsequent drying of the purified 2-mercaptobenzothiazole obtained may be carried out at a temperature of 20° to 100° C. and preferably at a temperature of 30° to 60° C., optionally under reduced pressure.

In another procedure, the crude 2-mercaptobenzothiazole is not completely dissolved, but only suspended, in the solvents mentioned above and in the following and is worked up in the same way as described above.

In addition to the solvents mentioned above, suitable solvents for suspending the crude 2-mercaptobenzothiazole include aliphatic or cycloaliphatic ethers, such as tert. butyl methyl ether, organic acids or esters thereof, such as acetic acid and acetic acid alkyl ester.

The solvent volume, the time and the temperature are preferably selected so that an optimal yield of high-purity product can be obtained. Complete dissolution of the crude melt of the 2-mercaptobenzothiazole is not necessary for obtaining a pure product.

The solvent is preferably used in a quantity of about 0.1 to 1.0 part by weight and, more preferably, in a quantity of 0.2 to 0.8 part by weight per part by weight crude 2-mercaptobenzothiazole used.

The suspension is stirred for about 10 minutes to 6 hours and preferably for 30 minutes to 2 hours. The temperature at which the suspension is treated is in the range from about 10° to 100° C. and preferably in the range from 30° to 80° C., but is always below the boiling temperature of the solvent or solvent mixture used.

The purified 2-mercaptobenzothiazole is recovered by filtration from the partly or completely cooled suspension, preferably at 20° C.

The 2-mercaptobenzothiazole purified by the process according to the invention is light yellow in color. The yields and purities obtainable are dependent on the solvent used and on the ratio of 2-mercaptobenzothiazole to solvent used.

The 2-mercaptobenzothiazole purified by the process according to the invention may be used, for example, as a vulcanization accelerator or as a corrosion inhibitor.

EXAMPLE 1

50 g crude melt of 2-mercaptobenzothiazole (purity:79.1%) are dissolved in 140 ml isopropanol at the boiling temperature under nitrogen as inert gas. The mixture is then left standing at room temperature to coo. The product precipitated is filtered off, washed with 20 ml isopropanol and dried. A light yellow product (yield: 69.8%, based on pure 2-mercaptobenzothiazole; 180.1° to 181.1° C.; purity:98.1%) is obtained.

EXAMPLE 2

50 g crude 2-mercaptobenzothiazole (purity: 79.1%) are recrystallized as in Example 1 from 130 ml of a mixture of 87.4% by weight isopropanol and 12.6% by weight water (azeotropic composition) under nitrogen as inert gas. The product precipitated is filtered off and washed with 20 ml of the isopropanol/water mixture. A light yellow product is obtained (yield: 73.8%, based on pure 2-mercaptobenzothiazole; Mp.:180.1° to 181.1° C; purity: 97.0%).

EXAMPLE 3

As in Example 1, 50 g crude 2-mercaptobenzothiazole (purity: 89.2%) are recrystallized from 39 ml n-butanol under nitrogen as inert gas. The product precipitated is filtered off and washed with 20 ml n-butanol. A light yellow product is obtained (yield: 84.7%, based on pure 2-mercaptobenzothiazole; Mp.: 179.9° to 181.2° C.; purity: 97.9%).

EXAMPLE 4

As in Example 1. 500 g crude 2-mercaptobenzothiazole (purity: 87.7%) are dissolved in 100 ml cyclohexanol under nitrogen as inert gas. The product precipitated after cooling is filtered off at room temperature and washed with 200 ml cyclohexanol. A light yellow product is obtained (yield: 87.8%, based on pure 2-mercaptobenzothiazole; Mp.: 180.5° to 182.0° C.; purity: 99.7%).

EXAMPLE 5

50 g crude 2-mercaptobenzothiazole (purity: 87.7%) are dissolved in 10 ml cyclohexanol at the boiling temperature. After cooling, the solution is filtered. The filter cake is then washed with 50 ml isopropanol. A light yellow product is obtained (yield: 86.5%, based on pure 2-mercaptobenzothiazole; Mp.: 180.8° to 182.0° C.; purity: 99.2%).

EXAMPLE 6

As in Example 5, crude 2-mercaptobenzothiazole (purity: 87.7%) is recrystallized from 10 ml cyclohexanol. The filter cake is washed with 50 ml of a mixture of 87.4% by weight isopropanol and 12.6% by weight water. A light yellow product is obtained (yield: 86.8%, based on pure 2-mercaptobenzothiazole; Mp.: 181.0° to 182.0° C.; purity: 99.1%).

EXAMPLE 7

As in Example 5, crude 2-mercaptobenzothiazole (purity: 87.7%) is recrystallized from 10 ml cyclohexanol and the filter cake is washed with 50 ml methanol. A light yellow product is obtained (yield: 83.9%, based on pure 2-mercaptobenzothiazole; Mp.: 181.0° to 182.8° C.; purity: 99.3%).

EXAMPLE 8

50 g crude 2-mercaptobenzothiazole (purity: 88.3%) are dissolved in 10 ml cyclohexanol at the boiling temperature and, after cooling of the solution to room temperature, the product precipitated is filtered off and immediately dried. A light yellow product is obtained (yield: 86.7%, based on pure 2-mercaptobenzothiazole; Mp.: 179.1° to 181.1° C.; purity: 97.2%).

EXAMPLE 9

As in Example 8, 50 g crude 2-mercaptobenzothiazole (purity: 88.3%) are recrystallized from 50 ml n-butanol. The product precipitated is filtered off and immediately dried. A light yellow product is obtained (yield: 84.0%, based on pure 2-mercaptobenzothiazole; Mp.: 179.1° to 181.0° C.; purity: 95.8%).

EXAMPLE 10

50 g crude melt of 2-mercaptobenzothiazole (purity: 91.0%) are stirred in 50 ml isopropanol for 30 minutes at 30° C. After cooling to room temperature, the residue is filtered off and dried. A light yellow product is obtained (yield: 92.1%, based on pure 2-mercaptobenzothiazole; Mp.: 181.8° to 182.1° C.; purity: 99.6%).

EXAMPLE 11

As in Example 10, crude 2-mercaptobenzothiazole (purity: 91.0%) is suspended for 1 hour in 50 ml isopropanol. A light yellow product is obtained (yield: 91.6%, based on pure 2-mercaptobenzothiazole; Mp.:181.8° to 182.1° C.; purity: 99.4%).

EXAMPLE 12

As in Example 10, crude 2-mercaptobenzothiazole (purity: 91.0%) is suspended for 1.5 hours in 50 ml isopropanol. A light yellow product is obtained (yield: 91.6%. based on pure 2-mercaptobenzothiazole; Mp.: 181.2° to 182.0° C., purity: 99.3%).

EXAMPLE 13

As in Example 10, crude 2-mercaptobenzothiazole (purity: 91.0%) is suspended for 2 hours in 80 ml isopropanol. A light yellow product is obtained (yield: 89.5%. based on pure 2-mercaptobenzothiazole; Mp.: 181.2° to 182.0° C., purity: 99.4%).

EXAMPLE 14

As in Example 10, crude 2-mercaptobenzothiazole (purity: 91.0%) is suspended for 3 hours in 50 ml isopropanol. A light yellow product is obtained (yield: 91.0%, based on pure 2-mercaptobenzothiazole; Mp.: 181.2° to 182.0° C.; purity: 100.0%).

EXAMPLE 15

As in Example 10, crude 2-mercaptobenzothiazole (purity: 87.7%) is suspended for 2 hours in a mixture of 87.4 % by weight isopropanol and 12.6% by weight water (azeotropic composition). A light yellow product is obtained (yield: 90.3%, based on pure 2-mercaptobenzothiazole; Mp.: 180.1° to 181.9° C.; purity: 98.8%).

EXAMPLE 16

As in Example 10, crude 2-mercaptobenzothiazole (purity: 87.7%) is suspended for 2 hours in 80 ml n-butanol. A light yellow product is obtained (yield: 82.4%, based on pure 2-mercaptobenzothiazole; Mp.: 181.1° to 182.1° C.; purity: 99.7%).

EXAMPLE 17

As in Example 10, crude 2-mercaptobenzothiazole (purity: 87.7%) is suspended for 2 hours in 50 ml cyclohexanol. A light yellow product is obtained (yield: 85.5%, based on pure 2-mercaptobenzothiazole; Mp.: 181.0° to 182.0° C.; purity: 98.8%).

EXAMPLE 18

As in example 10, crude 2-mercaptobenzothiazole (purity: 79.1%) is suspended for 2 hours in 50 ml tert.-butylmethylether. A light yellow product is obtained (yield: 90.5%, based on pure 2-mercaptobenzothiazole; Mp.: 180.5° to 182.0° C.; purity: 99.3%).

EXAMPLE 19

As in example 10, crude 2-mercaptobenzothiazole (purity: 79.1%) is suspended for 2 hours in 50 ml ethylacetate. A light yellow product is obtained (yield: 87.5%, based on pure 2-mercaptobenzothiazole, Mp.: 181.0° to 182.0° C., purity:99.4%).

EXAMPLE 20

As in example 10, crude 2-mercaptobenzothiazole (purity: 79.1%) is suspended for 2 hours in 50 ml concentrated acetic acid. A light yellow product is obtained (yield: 93.6%, based on pure 2-mercaptobenzothiazole; Mp.: 180.9° to 181.9° C.; purity:98.7%).

We claim:

1. A process for the purification of crude 2-mercaptobenzothiazole, characterized in that the crude 2-mercaptobenzothiazole is dissolved in relatively high-boiling aliphatic or cycloaliphatic alcohols or in mixtures of the alcohols mentioned or azeotropes thereof with water at temperatures of 60° C. to 200° C., optionally under elevated pressure, the solution is subsequently cooled and the product precipitating is filtered off and optionally washed.

2. A process as claimed in claim 1, characterized in that the alcohol is evaporated from the alcoholic solution of the crude 2-mercaptobenzothiazole obtained at temperatures of 60° to 200° C. and optionally under reduced pressure and the product precipitating is filtered off and optionally washed.

3. A process as claimed in claim 1, characterized in that the alcoholic solution of the 2-mercaptobenzothiazole which has been prepared under elevated pressure is expanded, the temperature is optionally reduced slowly to room temperature and the product precipitating is filtered off and optionally washed.

* * * * *